(12) United States Patent
Scott et al.

(10) Patent No.: US 7,229,977 B2
(45) Date of Patent: Jun. 12, 2007

(54) COMPOSITION FOR SOLUBLE FILMS WITH A NEW HYDROLYZED POLYSACCHARIDE

(75) Inventors: Robert Anthony Scott, Sint-Niklaas (BE); Dominique Cade, Colmar (FR); Xiongwei He, Andolsheim (FR)

(73) Assignee: Warner-Lambert Company, New York, NY (US)

( * ) Notice: Subject to any disclaimer, the term of this patent is extended or adjusted under 35 U.S.C. 154(b) by 0 days.

(21) Appl. No.: 10/868,302

(22) Filed: Jun. 15, 2004

(65) Prior Publication Data

US 2004/0265384 A1    Dec. 30, 2004

(30) Foreign Application Priority Data

Sep. 5, 2000    (EP) .................................. 00402437

(51) Int. Cl.
*A01N 25/26* (2006.01)
*C08B 37/00* (2006.01)
*A61K 9/24* (2006.01)

(52) U.S. Cl. .......................... 514/54; 514/55; 514/338; 514/313; 514/365; 536/18.6; 536/56; 536/84; 536/88; 536/123.1; 536/123.12; 536/55.1; 536/128; 435/252.1; 424/401

(58) Field of Classification Search .................. 514/55, 514/338, 373, 365, 547; 536/18.6, 56, 84, 536/88, 123.1, 123.12, 55.1, 128, 114; 435/252.1; 424/401

See application file for complete search history.

(56) References Cited

U.S. PATENT DOCUMENTS 4,306,059 A * 12/1981 Yokobayashi et al. . 536/123.12

FOREIGN PATENT DOCUMENTS

| GB | 2 223 503 | * | 4/1990 |
| GB | 2223503 | | 4/1990 |

OTHER PUBLICATIONS

Agnes Villain-Simonnet et al.; "A new bacterial polysaccharide (YAS34)"; Int. J. Biol. Macromol.; vol. 27, No. 1, 2000; pp. 65-75; XP002159348; Amsterdam; pp. 69; table 2.

Agnes Villain-Simonnet et al.; "A new bacterial polysaccharide (YAS34)"; Int. J. Biol. Macromol.; vol. 27, No. 1, 2000; pp. 77-87; XP002159349; Amsterdam; pp. 85-86.

* cited by examiner

*Primary Examiner*—Shaojia Anna Jiang
*Assistant Examiner*—Devesh Khare
(74) *Attorney, Agent, or Firm*—Steve Zelson; Rosemary Miano

(57) ABSTRACT

The invention is concerned with film-forming compositions containing hydrolysates of the exopolysaccharide YAS34 for the use in pharmaceutical, veterinary, food, cosmetic or other products like films for wrapping food, aspics or jellies, preferably for predosed formulations like soft or hard capsules.

14 Claims, No Drawings

COMPOSITION FOR SOLUBLE FILMS WITH A NEW HYDROLYZED POLYSACCHARIDE

This application claims priority under 35 U.S.C. § 120 to U.S. Application No. 10/344,117, filed Feb. 6, 2003 which claimed priority to PCT/EP01/09593, filed Aug. 21, 2001 and European Patent Application 00402437.8, filed Sep. 5, 2000.

The invention is concerned with film-forming compositions containing hydrolysates of the new exopolysaccharide YAS34 for the use in pharmaceutical, veterinary, food, cosmetic or other products like films for wrapping food, aspics or jellies, preferably for predosed formulations like soft or hard capsules.

A second embodiment of the invention is the use of the inventive composition for the manufacture of hard capsules by conventional dip molding process as normally used in the production of conventional hard gelatin capsules.

The new exopolysaccharide (EPS) is a bacterial polysaccharide "YAS34", produced by the soil bacteria *Rhizobium Leguminasorum* and developed under the trade name Soligel by ARD (Pomacle, France).

The repeating unit of YAS34 consisting of one glucuronic acid (GlcA), six neutral sugars of which 3 are galactoses (Gal) and 3 are glucoses (Glc), one pyruvate group and 1.6 acetate groups in average per unit (not located yet) is shown in scheme I:

the molecular weight and the viscosity of the aqueous solution viscosity. Furthermore the solubility of the polysaccharide film is significantly improved. Though some alterations of the mechanical properties have been observed, they remain at an acceptable level for the requirements of hard capsules.

The original polysaccharide YAS34 has a molecular weight of 1,400,000. An aqueous solution of 5% by weight gelatinizes at 60° C. and the the working temperature has to be above 60° C. for capsule manufacturing. If the concentration is increased to 10%, the working temperature has to be increased above 80° C. Such conditions are quite inconvenient and energy consuming for an industrial manufacturing process.

The hydrolysis of YAS34 under acid conditions is very efficient as demonstrated in experiments. Under the conditions given in example 1, within one hour, the molecular weight of the polysaccharide is reduced below 200,000 which can be used for the preparation of film-forming aqueous solutions with a content above 20%. Such solutions have acceptable viscosity even at room temperature. For this reason the molecular weight of the hydrolyzed YAS34 is preferably between 500,000 and 10,000 which allows the preparation of film-forming solutions in the range from 10 to 50% by weight.

Within the preferred Mw range the mechanical properties of the film remain quite acceptable even for hard capsule production.

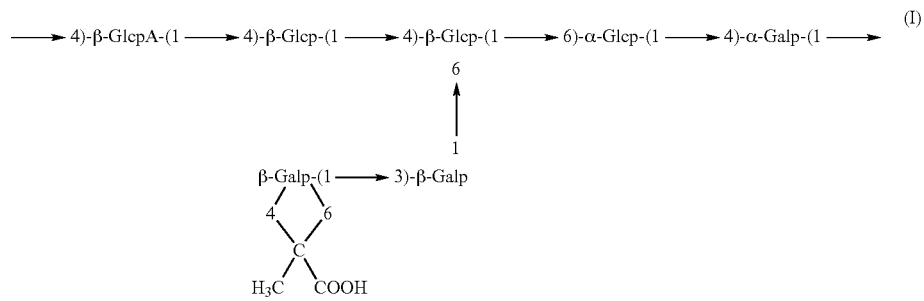

The production of YAS34 and the use as thickening agent, gelling agent, suspension agent, water retention agent, soil aggregation agent, texturing agent and seed coating agent is disclosed in WO98/35993.

YAS34 has a thermal reversible gelling ability and excellent properties for forming films with sufficient mechanical characteristics for the manufacturing of capsules, especially hard capsules. A disadvantage of the YAS34-films however is the poor water solubility at 37° C. It takes 50 minutes to dissolve a film of 100 μm thickness whereas a conventional gelatin film will be dissolved in only 2 minutes. A further disadvantage of YAS34 is its very high viscosity resulting from the very high molecular weight of the polysaccharide. But high viscosity and gelling ability result in the impossibility of forming films by casting or dip moulding, especially for hard capsules from solutions having an EPS concentration above 10%. Especially for the production of hard capsules high solid contents of the film forming aqueous solution are required. Low solid content will result in non-uniform film forming, long drying time and low productivity.

Surprisingly we have found that the disadvantages can be overcome by hydrolysis of YAS34, which reduces efficiently Conventional hard capsules are produced from gelatin by a dip moulding process. This process is based on the setting ability of hot gelatin solution by cooling. On a totally automatic industrial hard gelatin capsule machine, mould pins are dipped into hot gelatin solution, the pins are removed from the solution, inverted, the gelatin solution (gel) remaining on the pins dried, stripped off the capsule shells and finally cap and body of the capsules cut and pre-joined. The immediate setting of the gelatin solution on the mould pins after dipping is the key step in the process. Otherwise, the gelatin solution would flow down to form capsules with non-uniform wall thickness and unacceptable properties.

However the aqueous solution of the hydrolyzed polysaccharide YAS34 does not gelatinize at room temperature and does not have the necessary setting ability for hard capsule manufacturing by the described conventional dip moulding process. Surprisingly we have found that the addition of an additional setting agent to the aqueous solution or to the film-forming composition allows the adjustment and optimization of the setting ability of the solution to achieve uniform shell thickness of hard capsules.

Preferred setting agents for the inventive film-forming compositions or the aqueous solutions thereof are carrageenan, gellan gum, pectin, agarose, gelatin, xanthan with locust bean gum, xanthan with konjac, or unhydrolyzed YAS34. The preferred content of the setting agent in the solid film composition is 0.5% to 15% by weight. In the aqueous solution the setting agent is in the range of 0.05% to 5% by weight. Optionally the gelling agents are combined with mono or divalent cations like Calcium $Ca^{++}$ or $Mg^{++}$, e.g. water-soluble salts thereof, preferably in the aqueous solution in an amount of 0.01 to 3% or in the solid film composition in an amount of 0.1 to 5% by weight.

Aqueous solutions of the inventive film-forming composition containing hydrolyzed YAS34 and a setting agent and the films derived therefrom have following advantages:

High solid content which improves significantly the feasibility of different manufacturing processes.

Sufficient setting ability for hard capsule production by conventional dip moulding process.

High solubility of the films, suitable for predosed formulations such as hard capsules, soft capsules, tablet coating and ingredient packaging.

Acceptable mechanical properties of the films for hard capsules allowing filling and blistering operations.

The inventive composition may contain in a further aspect additional plasticizer, especially for soft film formulations such as soft capsules.

The inventive composition may contain in a further aspect additional coloring agents or flavoring agents.

The hard capsules of the invention may be used as containers for providing unit dosage forms, e.g. for agrochemicals, seeds, herbs, foodstuffs, dyestuffs, pharmaceuticals, flavouring agents and the like.

EXAMPLE 1

Hydrolysis of the Native Polysaccharide YAS34

15 g of YAS34 are dissolved in distilled water at 52° C. to form a solution containing 1.5% by weight to which 1000 ml 2M HCl are added under stirring. The mixture is incubated at 52° C. for A 1 hour and in a second batch B for 1.5 hours. After the given incubation time the solution is cooled to room temperature and neutralized to pH 7. The hydrolysates are precipitated with a water/ethanol (50/50 v/v) and washed 4 times with ethanol.

Molecular weights and viscosity of YAS34 and hydrolysates are shown in Table 1:

TABLE 1

|  | Mw average | Viscosity (cps) |
| --- | --- | --- |
| YAS34 | 1,400,000 | 5% at 50° C. gelatinized |
|  |  | 5% at 60° C. gelatinized |
| Hydrolysate A | 123,000 | 20% at 50° C. 650 |
| Hydrolysate B | 45,000 | 27% at 50° C. 300 |

The results in Table 1 demonstrate that hydrolysis under mild conditions efficiently reduces molecular weight and viscosity and the hydrolysates are well suitable for the preparation of aqueous solutions with acceptable viscosity and solid content for the manufacturing of hard or soft capsules.

EXAMPLE 2

Polysaccharide Films a) 50 g YAS34 are dissolved in distilled water at 90° C. to form a solution of 10% by weight After debubbling the solution was stabilized at 80° C. Films with a thickness about 100 μm were prepared by casting the solution on glass plates and drying at 22° C./50% RH over night.

b) 50 g hydrolysate B (Mw≈45,000) are dissolved in distilled water at 60° C. to form a solution of 27%. After debubbling, the solution was stabilized at 50° C. Films with a thickness about 100 μm were prepared by casting the solution on glass plates and drying at 22° C./50% RH over night.

The dissolution times of the films shown in Table 2 are determined according to UPS XXII dissolution test method conditions (at 37° C., in demineralyzed water).

TABLE 2

|  | YAS34 | Hydrolysate B | Gelatin |
| --- | --- | --- | --- |
| Dissolution (min) | 51 | 1.2 | 2.2 |

The mechanical properties of the films shown in Table 3 are determined by tensile tests with an Instron machine with films equilibrated by 50% RH at 22° C. before test.

TABLE 3

|  | YAS34 | Hydrolysate B |
| --- | --- | --- |
| Young's modulus (MPa) | 2400 | 2880 |
| Strength (MPa) | 59 | 55 |
| Elongation at break (%) | 19 | 9 |

The result of the tests demonstrate that hydrolysate B has a significantly higher dissolution rate than YAS34. The dissolution is even better than gelatin. The tensile strength of the hydrolysate is reduced when compared with YAS34 but the mechanical properties remain very acceptable not only for soft but even for hard capsule manufacturing.

EXAMPLE 3

Hard Capsules from Hydrolysate B 54 g hydrolysate B and 4 g of YAS34 are dissolved in distilled water at 70° C. to 200 g of a solution containing 27% hydrolysate B and 2% YAS34 by weight. After debubbling the solution was stabilized at 60° C.

The solution thus prepared was then poured into a dipping dish of a single pin pilot machine of conventional hard gelatin capsule production equipment. Hard capsules of size 1 were produced under similar conditions to hard gelatin capsule production. The produced hard capsules have similar dimensions to the conventional gelatin hard capsules.

The produced hard capsules were evaluated by disintegration tests according to USPXXIII at 37° C. in demineralized water:

| First leak: | 1.4 minute |
| --- | --- |
| Total disintegration: | 9.5 minutes |

The invention claimed is:

1. A film forming composition capable of forming hard capsules with uniform thickness, the composition comprising an aqueous solution, 10–50% by weight (based on the aqueous solution) of hydrolyzed exopolysaccharide EPS YAS34 and a setting agent.

2. The composition according to claim 1, wherein the EPS YAS34 is hydrolyzed to an average molecular weight range from 500,000 to 10,000 Daltons.

3. The composition according to claim 2, wherein the hydrolyzed EPS YAS34 has an average molecular weight of 45,000 Daltons.

4. The composition according to claim 1, wherein the setting agent is selected from the group consisting of carrageenan, gellan gum, pectin, agorose, gelatin, xanthan with locust bean gum, xanthan with konjac, native EPS YAS34, and mixtures thereof.

5. The composition according to claim 1, wherein the setting agent comprises 0.5–15% by weight of the composition.

6. The composition according to claim 1, wherein the setting agent comprises a salt of a mono or divalent cation.

7. The composition according to claim 6, wherein the cation salt comprises 0.01 to 5% by weight of the composition.

8. A capsule for unit dosage forms comprising the composition according to claim 1.

9. The composition according to claim 1, wherein the aqueous solution comprises hydrolyzed EPS YAS34 in an amount of 10 to 50%, by weight of the aqueous solution.

10. The composition according to claim 1, wherein the aqueous solution comprises hydrolyzed EPS YAS34 In an amount of 15 to 40%, by weight of the aqueous solution.

11. The composition according to claim 1, wherein the aqueous solution comprises a setting agent in an amount of 0.01 to 5%, by weight of the aqueous solution.

12. The composition according to claim 11, comprising hydrolyzed EPS YAS3S in an amount of 0.03 to 3% by weight, of the aqueous solution.

13. The composition according to claim 11, wherein the aqueous solution comprising a salt of a mono or divalent cation in an amount of 0.01 to 3% by weight of the aqueous solution.

14. The composition according to claim 13, wherein the aqueous solution comprises a salt of a mono or divalent cation in an amount of 0.01 to 1%, by weight of the aqueous solution.

* * * * *